United States Patent [19]

Larson

[11] 4,006,542
[45] Feb. 8, 1977

[54] SHOE INSOLE OF A SOLID CRYSTALLINE POLYMER

[75] Inventor: Lester M. Larson, Wilmington, Del.

[73] Assignee: Larson Corporation

[22] Filed: Nov. 4, 1974

[21] Appl. No.: 520,730

[52] U.S. Cl. .................................. 36/43; 36/44;
2/410; 128/90; 428/43; 428/137; 428/138;
428/510; 260/894; 260/890; 264/230;
526/295; 526/335

[51] Int. Cl.² .................. A43B 13/38; B32B 27/06

[58] Field of Search .................. 161/112, 113, 247;
36/43, 44; 260/17.4, 894, 890; 264/222, 230;
428/510, 43, 137–138; 526/295, 335

[56] References Cited

UNITED STATES PATENTS

| | | | |
|---|---|---|---|
| 3,244,649 | 4/1966 | Levitt | 36/43 X |
| 3,266,178 | 8/1966 | Gilkerson | 36/43 |
| 3,442,031 | 5/1969 | Antell | 36/43 X |
| 3,734,814 | 5/1973 | Davis et al. | 161/112 |
| 3,853,796 | 12/1974 | Oldack et al. | 260/17.4 BB X |
| 3,855,379 | 12/1974 | Araki et al. | 260/17.4 BB X |

Primary Examiner—P. C. Ives

[57] ABSTRACT

Heat softened polydienic sheets, such as transpolyisoprene or polychloroprene, are usefully mounted in rolls, the layers being separated by powders or granules such as salt to prevent cohesion, and the salt is preferably dusted off as used, or the sheet is passed through a warm water bath which will remove the salt and warm it and softening to an applying state useful for many purposes. It can be shaped as an in-sole for shoes and upon softening will accept the shape of the wearer's foot greatly improving the comfort; or as breast plates, athletic supporters, knee guards, head guards such as a helmet, ear guards or ear supports which may carry sound transfer means, i.e., such as headphones or a hearing aid; or it may be used as a bandage and for which purpose it can be reinforced by a long fiber and the comfort of the plastic bandage can be modified as by having perforations filled with fiber to transmit moisture from side to side.

8 Claims, 12 Drawing Figures

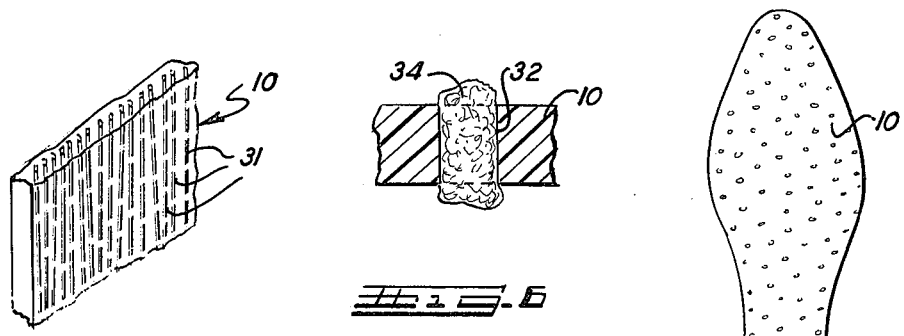
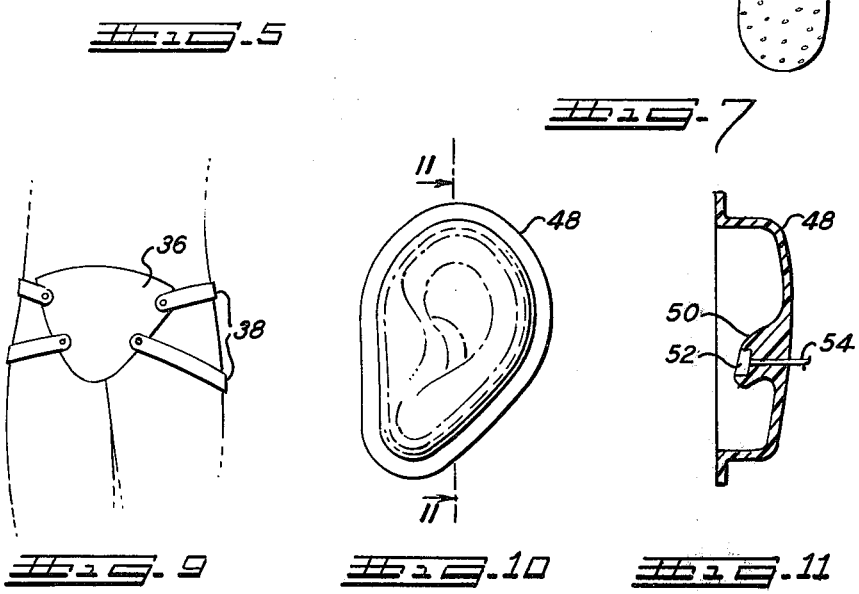
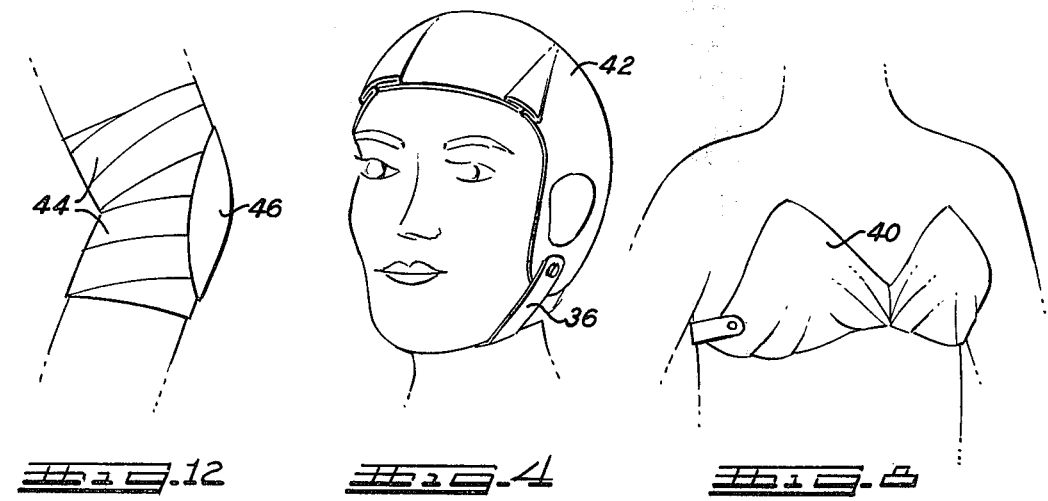

SHOE INSOLE OF A SOLID CRYSTALLINE POLYMER

This invention relates to improved materials for forming molded body supporting casts, splints or protective elements for body parts such as helmets, shoes, brassieres, belts, athletic supporters, headphones, ear plates and plugs or the like; including the formation of moldable plastic storable in rolls, stacks or sheets or moldings from which individual moldable elements are readily separated and formed into shapes for such uses; and to methods for modifying the heat softening characteristics for the specific uses as listed and for improving the strength and aeration characteristics for such use.

This invention is an improvement over my prior application, Ser. No. 683,016, filed Nov. 14, 1967, now U.S. Pat. No. 3,490,444, and a continuation-in-part of co-pending application, Ser. No. 3,474 now U.S. Pat. No. 3,809,600 co-pending with said patent, and a continuation-in-part application, Ser. No. 385,914, now U.S. Pat. No. 3,853,124 in that the sheets or layers of heat softenable plastics, heated above normal comfortable body temperatures and controllably settable by crystallization at or upon cooling below about body temperatures, are assembled in a readily dispensable manner before or after heating for uses listed above.

In one outstanding end use a heat softenable polydiene, typically crystallizable transpolyisoprene, transpolychloroprene, transpolybutadiene, and mixtures thereof with each other and with other thermoplastic substances, useful for modifying the setting and softening characteristics of said polymers, the controlled plastic body, preferably adjusted in composition to a selected softening and setting temperature, has its surfaces cohesion properties modified by dusting with solid particles, preferably water-soluble particles such as water-soluble salt crystals, operative as a separating agent to inhibit the cohesion between sheets for easy handling and storage to be easily separable sheet by sheet. The dust-like particles are easily removed by dusting, and ready cohesion between the plastic sheets surface to surface is restored by heating at the softening temperature whereby the plastic bodies are quickly and easily stored and then used with effective cohesion for any of the listed purposes.

In a second aspect of the invention, the plastic bodies are formed or cut into narrow strips of a width selected for the end use intended and may be assembled in rolls, one surface coated with said solid dust separator particles, whereby they will not cohere in storage and the strips are easily separated. In such rolls, one preferred use will be as a splint or body supporting cast formed by wrapping the heat softened plastic about the body member or body trunk as a bandage, in which the original roll is preheated for softening, or in which the hardened roll is unwound and passed through a warm water bath, thus easily removable by dissolving the water-soluble salt. Most of the dust-like surface protective materials either are removable by dusting and do not need further removal for use, but it is preferred to dissolve them in the warm water bath in which the bandage-like plastic is passed for heat softening.

The heat softened continuous strip is preferably used as a bandage and wrapped around the body member to be protected, and will set at a comfortable contact with the body at about body comfort temperature such as around 40° C in a short period of time to a protective cast thereabout, the heat softened surfaces cohering to each other. It will be useful for such body member to be reinforced by fiber as taught in my patent, referred to above, preferably using long fibers running as parallel strings inlaid in the plastic to convert the bandage-like strip into a strong cord or fiber reinforced belt, resistant to substantial tension for numerous specific uses wherein tension in a bandage is desirable. Such fiber may be several wound or spun into a yarn, string or cord, but the fiber may be fine hollow tubes extruded from plastic to impart both strength as well as porosity to the sheet; such fiber can vary from fine capillary to larger tubes, that is, about 1/32 inch up to about ⅛ inch in diameter.

In further aspect of the invention, the strips of the plastic may be cut into flat shapes useful as a shoe member, typically an inner sole, insertable within a shoe. When ready for sale or use, the sole is warmed and softened in which condition the shape of the foot of the user may be inserted in the shoe and pressed down on the softened inner sole, deforming it to the exact optimum comfortable shape of the user's foot, in which form the inner sole will be allowed to set. This provides a comfortable walking sole which exactly fits the user's foot.

In another aspect, the plastic, in contrast to a continuous unwindable roll, may be in the form of sheets stacked in a tier and separated by particulate matter for ready separation and use. Such sheets, of course, can also be protected, as shown in my prior patent, by a protective sheet or wrapper which is first removed. The sheet may be warmed and wrapped around a foot of the user for use as temporary footwear as in swimming, temporary house slippers, a type of walking cast for an injured foot, and the like. In such use, the outer dimensions or shape of the sheet is not significant and a large rectangular sheet, strip or plate, after softening with heat, may be deformed and mounted about the foot, and the excess plastic material may then be trimmed away by a pair of scissors, or the trimming away may be applied to the rectangular softened sheet just prior to forming about the foot as desired.

In a further desired use, generally on a temporary basis and just prior to the useful need, a sheet of the heat warmed plastic may be molded about a user's head, hands, knees, elbows, or other body parts, such as a helmet, or knee or elbow guard, heated, shaped and formed just prior to some athletic event by a user needing that kind of immediate temporary protection.

In a similar way, the softened sheet can be deformed by the user into an athletic supporter or brassiere molded about one or more breasts or genitals, protective against injury prior to an athletic event such as wrestling, running, jumping, soccer, fencing, judo, or the like, protective for the user before engaging in a potentially dangerous activity.

In the several uses for substantial periods or even temporarily prior to anticipation of possible injury, the heat softenable plastic is applied after softening and molding to or about the body member and the bandage, tape or sheet is held at about body temperature until crystallization of the polymeric substance is effected and the plastic sets hard and will protect the body by resisting impact of the type encountered in numerous sports in which active participation is involved.

The polymers as listed above are generally crystallizable. That is, when heated they will generally soften to an amorphous plastic form, and then will set by recrystallization on cooling. Particularly preferred among the plastics listed are the transpolyisoprene and transpolychloroprene and their mixtures with others listed in which one of these polymers is a predominant or at least a very substantial component such as 25% or more. The polymer on heating to soften such as above about 60° C will exhibit on cooling a modified hystersis, variable with the softening temperature to which the product was heated to effect softening in the range of 60° to 110° C. The higher the temperature to which the polymer is heated in the said range to effect the softening, the greater hysteresis and longer time delay period will result to effect substantial recrystallization, that is, hardening. For instance, when the transpolyisoprene is heated to a decrystallization temperature of only 55° C and then cooled, it will harden in about a minute at 40° C. Thus, at this very low softening temperature to which it was heated it resets very rapidly to a rigid form. When the same transpolyisoprene is heated to 70° C and then cooled to 40° C, it will remain soft for several times that period, at least 6 minutes, before setting to a firm set. Finally, as the same transpolyisoprene is heated to a 100° C then cooling to a same 40° C, it will require at least 13 minutes to take on a firm set at the lower 40° C temperature. That type of tempering by heating to a softening temperature higher and higher above the minimum, for instance, above 60° C, and within the stated range, allows the user to build into the polymer sheet a selected and convenient cold setting time as needed, that is, to take advantage of the inherent hystersis of the crystallizable polymer available by heating to the selected higher temperature to incorporate a desirable setting time, as is useful in the particular molding.

This invention is further described in relation to the drawings wherein:

FIG. 4 illustrates a deformation of the heat softened material in the form of a helmet;

FIG. 5 is a modified form of the plastic sheet having long string-like fibers to enhance the strength and porosity of the sheet of polymer;

FIG. 6 is an enlarged detail showing perforations in a sheet with fiber filling the perforations;

FIG. 7 is an inner sole fittable in a shoe and moldable to the contours of the bottom of a foot;

FIG. 8 illustrates shaping of the polymer as breast plates;

FIG. 9 illustrates shaping of a polymer as an athletic support;

FIG. 10 is a plate shaped as an ear guard or earphone;

FIG. 11 is a section through FIG. 10 in elevation taken on the line 11—11 of FIG. 10; and FIG. 12 is a plate shaped as a knee guard.

Figure 1:
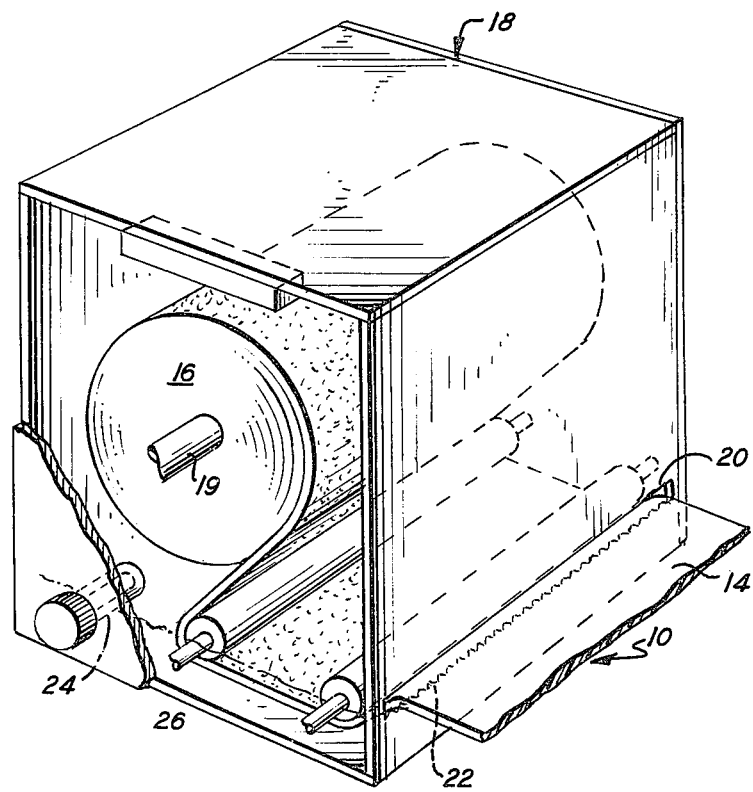
FIG. 1 illustrates a roll of plastic having means for heating the roll to a softening temperature.

As shown in FIG. 1, a sheet of heat softenable polymer such as transpolyisoprene or transpolychloroprene 10 usually formed has its surface 12 dusted with granules of salt 14 at a temperature of about 60° C at which it is soft and the strip 10 is rolled spirally into a roll 16 so that the contiguous layers 15 and 17 of the roll upon unwinding are easily separable, the crystals 14 being loose are applicable and removable merely by dusting on or from the surface 12. Such water soluble salts do not tend to be wetted by or cohered to the organic plastic surface either in the hardened or softened state and make a superior plastic separating layer of nonadherent particles so that the plastic surfaces 12 in the roll 16 separated by salt granules do not cohere to each other in storage.

The roll 16 is mounted in a dispenser 18 for unwinding about an axle 19, unrolling as a sheet of plastic dispensed through an opening 20 which has a sharp edge cutting surface 22 upon which measured strips may be torn or cut as they are separated from the continuous strip 10 at any selected length. Heating elements 24 are mounted in the walls of the dispenser which will warm a lower hot water layer in the interior thereof. The temperature of the water is maintained by a resistor thermostat 29 to heat the water selectively above 60° C, whereby the roll of the plastic strip is maintained in the softened state ready for use. The chamber 24 may be dry, merely supplying heat and the separated strip may be hand dusted to remove the salt or alternately dipped in the warm water bath 24 to dissolve the salt dust from the surface. The softened sheet is then wrapped alternately around an injured body member as a cast or splint, and upon removal of the salt, any overlapping edges will adhere to each other. The wrapped bandage-like strip film will set as a body supporting cast or splint after cooling to a comfortable temperature for the body in a selected short period of time of about 2 to 20 minutes, variable as desired by heat tempering as described above.

Figure 2:
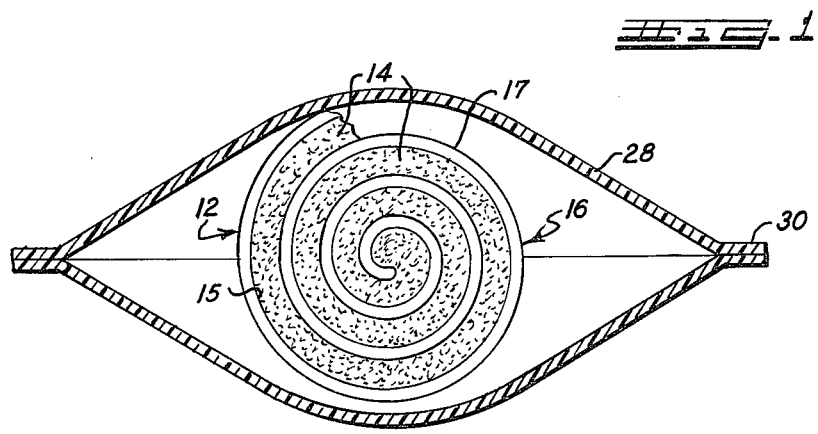
FIG. 2 is a section through the roll in packaged form.
Figure 3:
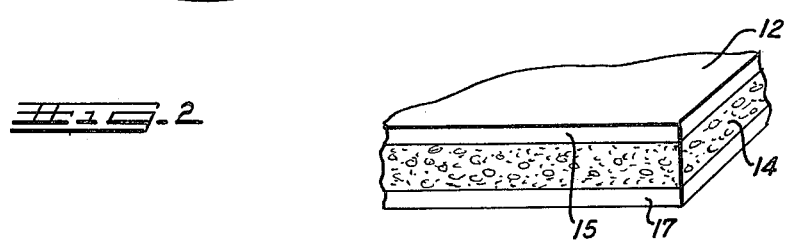
FIG. 3 is a detail of two roll layers.

As shown in FIG. 2, the coiled plastic 12 having its laminar surfaces 15 and 17 separated by dusted salt particles 14 may be enclosed in the sealed wrapper 28 of the disposable plastic film such as polyethylenes which preserves the softenable plastic sheets from oxidation in air. In use, the wrapper may be torn at the sealed edges 30, removed and the coil, then will be inserted in the dispenser as shown in FIG. 1, first inserting the supporting axle 19. It may be useful to use the coil of FIG. 2 by heat softening the entire coil in a warm water bath without a dispenser, and then apply the soft plastic bandage like roll to a body part, merely brushing off, washing or sponging off the loose salt particles as the softened plastic film is applied such as wrapping around the body part. It will be understood that the salt particles 14 as shown in FIG. 3 merely serve to separate adjacent sheets 15 and 17 preventing their cohesion in storage. That salt is easily dusted off and will not wet the heat softenable plastic whereby it may be either dusted off, or washed off in a water bath, usually by being merely removed by dusting, mechanically brushing.

As shown in FIGS. 5 and 6, a plastic sheet 10 may have elongated fibers 31 and perforations 32 in its surface, fairly close spaced as needed, for the purpose of providing optimum body comfort, since such perforations in the plastic will allow moisture evolved to pass from one side of the sheet to its opposite side to enhance that moisture passage and consequent comfort to the enclosed body member. Each perforation 32 may have a wad or strand of fiber 34 inserted which serves as a wick to allow easier passage of mositure through the perforation or to pass liquid moisture or gaseous vapor.

As shown in FIG. 7, a strip 10 may have its outer contour sized and shaped as an inner sole of a correspondingly sized shoe capable of fitting within such shoe variable over a range of two or three or a usual selected number of sizes. The inner soles may be assembled in rolls 16 as in FIG. 1., each suitable to dispense an inner sole useful in the selected range of sizes so that a shoe store may have several rolls covering an entire range of shoe sizes. Upon sale of a pair of shoes, a heat softened pair of inner soles are drawn from the roll 16 through the FIG. 1 dispenser, each inner sole then being inserted within the pair of shoes. The purchaser then will insert the shoes upon his feet, deforming the surface heat softened plastic inner sole to conform to his own foot, whereby in a new pair of shoes the inner sole is shaped to fit the foot of the purchaser in a condition of optimum comfort. The plastic bodies listed have enough inherent flexibility to accommodate normal inner sole flexibility needed in walking, but the present inner sole exactly molded to the foot of the user will provide optimum comfort.

In a similar manner, a person anticipating body stress in any physical activity or one who already has injured body parts which need protection may separate a strip of desired length from the roll and wind it about the body as a guard or protective belt reinforced as desired by long fibers 31, protective of the portion for which it may be needed.

Similarly, a sheet or strip may be heat softened and mounted about any body member as an athletic supporter 36 as shown in FIG. 9, supplying additional flexible straps 38 to maintain the supporter 36 in place; or such plastic sheet may be shaped as breast plates 40, similarly fastenable with additional straps 36 to the body, the molded shapes held in place in a desirable form fit upon a woman's breasts, as shown in FIG. 8. The molded body part of plastic may also be supported in place as a hard plate-like filler or insert within or without a normal body-supporting element such as a bra or athletic supporter made in part of fabric and supporting the hard molded plastic sheet shaped exactly and comfortably sized to the body element as an insert within the normal fabric supporter.

Of course while it is useful to handle the roll 16 as such or separable plates of cohesive plastic in a dispenser 18 as described, such rolls may be warmed independently in the container of FIG. 3 by the user, first stored in its hardened state, and then warmed in a heated water bath to condition it to pliable softness before or after unwinding a roll as softened plastic to be molded to the body part.

In a similar manner, as shown in FIG. 4, the plate 42 after softening may be shaped to the user's skull or head as a helmet with or without a sheet of fabric or plastic foam as a comfort imparting inner-liner (not shown), whereby it forms a hard set outer plate or protective shield, comfortably and exactly fitting the head of the user after soft forming and setting. That helmet may be further secured to the head of the user with a flexible chin strap 36.

Again, as shown in FIG. 12, it may be useful, in applying an ordinary flexible elastic bandage 44, to secure a heat softened moldable plastic sheet 46 as described hereinabove to the knee as a knee cap or protective plate; or to the elbow as an elbow guard for temporary use in sports, as a protective member for these parts for the user as a temporary guard. That molding of course can be used again by the same person, but by this manner, molded to an individual for personal exact fit.

Again, as shown in FIGS. 10 and 11, ear pieces 48 may be shaped to fit an ear protectively, and each may even have an inner portion of softened moldable plastic fitted within the ear passage at 50. These protective devices may be useful ear coverings merely for swimming, or to prevent ear damage in various athletic activities. Since the molding is of optimum fit and individual comfort, shaped to each individual ear for this purpose, it may also be used for support for an earphone having an electrically operated sound diaphram 52 connected to a sound actuating wire 54 for inducing sound as an ordinary earphone into the ear with an individually shaped support for each user.

As indicated above, each of the devices shown may have perforations and may carry fabric in each perforation for transfer of moisture, thereby including optimum fit and comfort for the user. Some of the devices may be used in combination, for instance, the helmet of FIG. 4 may have an ear piece 48 molded in the sheet of the type shown in FIGS. 10 and 11 for optimum use of the helmet, in obvious comfort for the ears of the wearer.

The temperature of actual softening and setting as well as the time of hardening may be modified somewhat by blending of polydiene polymer with other compatible crystalline polymeric substances which will crystallize or at least begin to crystallize at a somewhat higher temperature than the low heat softening polymer transpolyisoprene or transpolychloroprene as suggested above. For this purpose, the dienic polymer may be blended with such substances as transpolybutadiene, polystyrene, polymethylstyrene, and the like polymeric substances which set to crystalline form at a temperature substantially above that of the lower melting transpolyisoprene or transpolychloroprene. These higher melting crystalline polymeric substances to be added in relatively small quantity to the low melting polymers such as less than about 10% by weight, typically 1 to 5%, a quantity controlled more or less in that range to adjust the melting point of the low melting polymer to that described.

Moreover, in this practice of varying the melting point by adding higher melting polymeric substances, it is possible to adjust the rate of polymerization of the low melting polymer merely because the higher melting polymer, first to begins to crystallize tends on incipient crystallization, to accelerate the crystallization of the lower melting polymer. In contrast to this, the low melting polymer such as transpolyisoprene or transpolychloroprene develops a hysteresis, a time lag, in which it resists crystallization, particularly around the body temperature such as 38° to 42° C, whereby the low melting polymer may be cooled substantially below body temperature before it will set with a substantial time lag of a few minutes up to 15 to 20 minutes because of the hysteresis.

That time lag as noted above can be selectively varied by increase of the temperature to which the polymer is heated, the higher temperatures giving progressively higher time lags. Conversely, the added content of high melting polymer tends to also reduce the time lag adjustably as desired. Thus, it will be noted that the amount of time lag can be adjusted in both directions.

The following example illustrates the preparation of a strong, heat softenable bandage usefully applied as a body member in tension.

EXAMPLE I

Transpolyisoprene is first blended with 1% of transpolybutadiene whereby its normal softening temperature is unchanged from the usual 60° C, but it will set in about a minute or two after cooling to around body temperature about 40° C. The said polymer mixture has incorporated therein long strands of glass fiber for imparting a substantial tensile strength, as shown in FIG. 5. Its surface is dusted with ordinary salt granules heated to about 65° C and then rolled into a roll for a potential use as a bandage having a width of about 4 inches and being about 6 feet long. It is enclosed in a package and stored cold until ready for use for example in a physician's office as shown in FIG. 2. The rolled bandage is then placed in a dispenser as shown in FIG. 1 and warmed to 65° C dispensed in strips drawn at the desired length and wrapped in judiciously applied tension by the physician around an injured body member and held at the body temperature for 2 minutes, whereby it sets rigid.

In a similar manner, the plastic in sheets are shaped as inner soles and used as shoes. Other sheets, either a flat plate or dispensed in a roll, are molded to various body parts as shown.

Certain modifications will occur to those skilled in the art and, accordingly, it is intended that the above description be regarded as illustrative and not limiting except as defined in the claims appended hereto.

What is claimed is:

1. A shoe insole comprising a heat deformed sheet of solid crystalline polymer of a solid polyolefinic compound, selected from the group consisting of transpolyisoprene, polychloroprene and each of said polymers with polybutadiene heat softenable at about 60° C and higher and hardenable by crystallization to rigid hardness upon cooling to about 40° C, said polymer being formed into a sheet sized and shaped to fit as an insole in a shoe and molded in its heat softened state at a body comfortable temperature to at least a portion of the wearer's foot.

2. A shoe insole as defined in claim 1, wherein the insole polymer is transpolyisoprene and extends over a substantial portion of the foot of the wearer.

3. A shoe insole comprising a polymer of a solid, crystalline, heat softenable compound, heat softened at about 60° C and higher and hardenable by setting with a time delaying hysteresis to recrystallize to rigid hardness upon cooling to about 40° C, said polymer being formed into a sheet and shaped and sized as an innersole to fit within a shoe, said innersole being moldable in its heat softened state to at least a portion of the wearer's foot and retaining said foot impression upon setting.

4. A shoe insole as defined in claim 3 wherein said polymer is a solid crystalline polyolefinic compound, selected from the group consisting of transpolyisoprene, polychloroprene and each of said polymers with polybutadiene.

5. A shoe insole as defined in claim 3, having perforations distributed close spaced in a pattern throughout a substantial portion of its surface and extending from surface to surface.

6. A shoe insole as defined in claim 5, wherein the perforations have tufts of fiber inserted therein.

7. A shoe insole as defined in claim 3, wherein the polymer sheet has elongated fibers distributed throughout its body.

8. A shoe insole as defined in claim 7, wherein the polymer sheet has perforations distributed in a pattern through its body and the perforations have tufts of fiber inserted therein.

* * * * *